United States Patent
Brown et al.

(10) Patent No.: US 7,062,091 B2
(45) Date of Patent: Jun. 13, 2006

(54) COORDINATE CALIBRATION FOR SCANNING SYSTEMS

(75) Inventors: Carl S. Brown, Seattle, WA (US); Ray H. Kraft, Seattle, WA (US); John Timothy Strom, North Bend, WA (US); Mark D. Cavelero, Everett, WA (US)

(73) Assignee: Applied Precision, LLC, Issaquah, WA (US)

( * ) Notice: Subject to any disclaimer, the term of this patent is extended or adjusted under 35 U.S.C. 154(b) by 229 days.

(21) Appl. No.: 10/047,458

(22) Filed: Jan. 14, 2002

(65) Prior Publication Data

US 2002/0097898 A1     Jul. 25, 2002

Related U.S. Application Data

(60) Provisional application No. 60/262,000, filed on Jan. 16, 2001.

(51) Int. Cl.
*G06K 9/32*     (2006.01)

(52) U.S. Cl. .................. 382/195; 382/291; 382/293; 358/486; 358/488

(58) Field of Classification Search ............... 382/128, 382/151, 206, 216, 218, 219, 278, 282, 284, 382/287, 291, 293, 294, 295, 307, 112, 113, 382/129, 133, 275, 315; 345/648, 651, 655, 345/656, 641; 358/450, 452, 453, 486, 488, 358/496; 250/363.07, 363.09, 370.01
See application file for complete search history.

(56) References Cited

U.S. PATENT DOCUMENTS

| | | | | |
|---|---|---|---|---|
| 4,760,385 | A | * | 7/1988 | Jansson et al. ............. 340/709 |
| 4,941,082 | A | * | 7/1990 | Pailthorp et al. ............. 700/57 |
| 5,018,209 | A | * | 5/1991 | Bacus ........................ 382/129 |
| 5,047,646 | A | * | 9/1991 | Hattori et al. .......... 250/396 R |
| 5,050,112 | A | * | 9/1991 | Hedglen et al. ............. 702/152 |
| 5,260,578 | A | * | 11/1993 | Bliton et al. ............. 250/461.1 |
| 5,354,992 | A | * | 10/1994 | Thompson et al. ......... 250/548 |
| 5,365,074 | A | * | 11/1994 | Genovese ............. 250/559.29 |
| 5,382,806 | A | * | 1/1995 | Bacchi et al. .......... 250/559.29 |
| 5,446,545 | A | * | 8/1995 | Taylor ........................ 356/501 |
| 5,499,097 | A | * | 3/1996 | Ortyn et al. ................. 356/615 |
| 5,687,251 | A | * | 11/1997 | Erler et al. .................. 382/133 |
| 5,694,212 | A | * | 12/1997 | Weissman ................ 356/237.1 |
| 5,787,208 | A | * | 7/1998 | Oh et al. ..................... 382/257 |
| 5,825,670 | A | * | 10/1998 | Chernoff et al. ............. 702/85 |
| 6,185,444 | B1 | * | 2/2001 | Ackerman et al. .......... 600/410 |
| 6,272,235 | B1 | * | 8/2001 | Bacus et al. ................. 382/133 |
| 6,485,413 | B1 | * | 11/2002 | Boppart et al. ............. 600/160 |
| 6,504,608 | B1 | * | 1/2003 | Hallmeyer et al. ......... 356/369 |
| 6,699,627 | B1 | * | 3/2004 | Smith et al. .................. 430/22 |

* cited by examiner

*Primary Examiner*—Jayanti K. Patel
*Assistant Examiner*—Yosef Kassa
(74) *Attorney, Agent, or Firm*—Pillsbury Winthrop Shaw Pittman LLP

(57) ABSTRACT

A scanning system is calibrated to correct for possible panel misalignments errors. A reference slide or data point is used to obtain a series of measurements with the scanning system. These measurements are compared with the expected results to determine systematic alignment errors in the scanning system. A model is created to correct the alignment errors during the scanning process, thus providing a plurality of more accurate scans. The plurality of scans may then be assembled to create a complete image of the scan area.

20 Claims, 6 Drawing Sheets

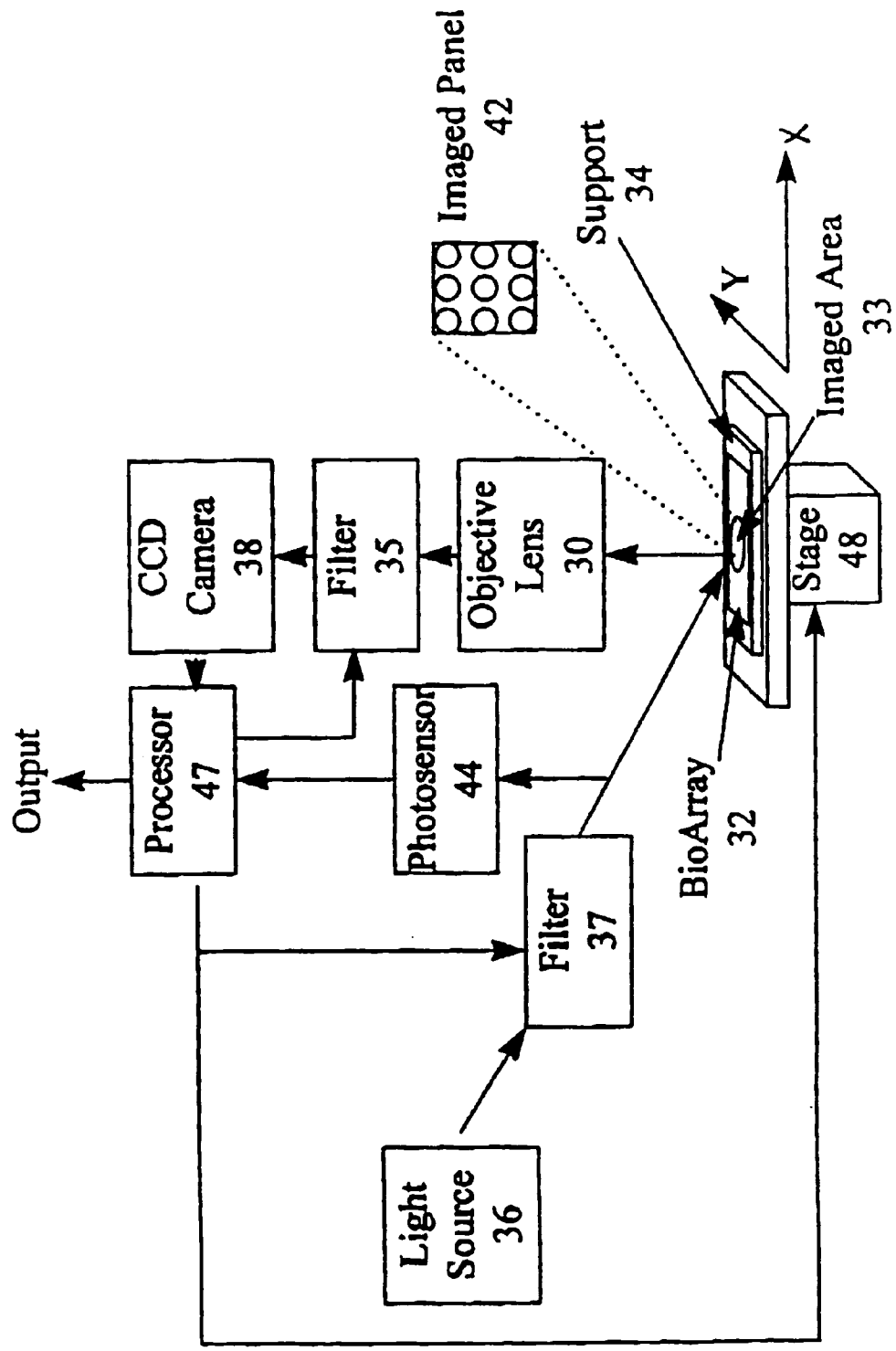

COORDINATE CALIBRATION FOR SCANNING SYSTEMS

CROSS-REFERENCE TO RELATED APPLICATIONS

This application claims priority to U.S. provisional Application Serial No. 60/262,000, filed on Jan. 16, 2001, the contents of which are incorporated by reference herein.

TECHNICAL FIELD

This invention relates generally to detection of high content field information such as arrays of small biological specimens, and more specifically concerns calibration of the camera and stage to optimize performance.

BACKGROUND

Biomedical research has made rapid progress based on sequential processing of biological samples. Sequential processing techniques have resulted in important discoveries in a variety of biologically related fields, including, among others, genetics, biochemistry, immunology and enzymology. Historically, sequential processing involved the study of one or two biologically relevant molecules at the same time. These original sequential processing methods, however, were quite slow and tedious. Study of the required number of samples (up to tens of thousands) was time consuming and costly.

A breakthrough in the sequential processing of biological specimens occurred with the development of techniques of parallel processing of the biological specimens, using fluorescent marking. A plurality of samples are arranged in arrays, referred to herein as microarrays, of rows and columns into a field, on a substrate slide or similar member. The specimens on the slide are then biochemically processed in parallel. The specimen molecules are fluorescently marked as a result of interaction between the specimen molecule and other biological material. Such techniques enable the processing of a large number of specimens very quickly.

A significant challenge exists in the scanning of such microarrays, due to their very high content, the relatively large size of the field, and the requirement of very high optical resolution of the scanning system due to the small size of the specimens. An improved system and method for scanning a plurality of specimens arranged within a scan area on a substrate, such as a slide, was presented in co-owned U.S. patent application Ser. No. 09/289,799 filed Apr. 9, 1999. In that application, a system was disclosed wherein successive portions of an array of small biological specimens are imaged using a CCD camera. The x,y coordinates of each successive portion within the array are also determined. The array is moved by a precision staging system to accurately locate each successive portion in the array. The separate data portions are then arranged together using the coordinates of each portion to produce a complete data image of the array, without any geometric adjustment or matching necessary between successive portions.

These scanning systems require high precision in the location of the staging area relative to the camera. When errors are introduced between the staging area and the camera, the precise location of each data portion may vary slightly, thereby making the arrangement of the image portions more difficult. What is needed is a system that detects any systematic alignment errors and compensates for these errors prior to assembling the complete image.

SUMMARY

Accordingly, the present invention calibrates a scanning system to correct for panel misalignments errors. A reference slide or data point is used to obtain a series of measurements with the scanning system. These measurements are compared with the expected results to determine alignment errors in the scanning system. A model is created to correct the alignment errors during the scanning process, thus providing a plurality of more accurate scans. The plurality of scans may then be assembled to create a perfectly registered, complete image of the scan area.

DESCRIPTION OF DRAWINGS

FIG. 1 is a diagram showing the arrangement of the scanning system of the present invention.

DETAILED DESCRIPTION

The present invention uses a high content material, such as a microarray extending over a relatively large area (up to 2-½ inches square) which is accurately scanned with high resolution as shown in FIG. 1. An objective lens 30, with high resolution and high light collection efficiency characteristics, is used to detect the data in successive small portions (panels) of the microarray field 32 present on substrate 34. An example of such a lens is a Nikon 4X objective with a 0.2 NA.

Figure 3:
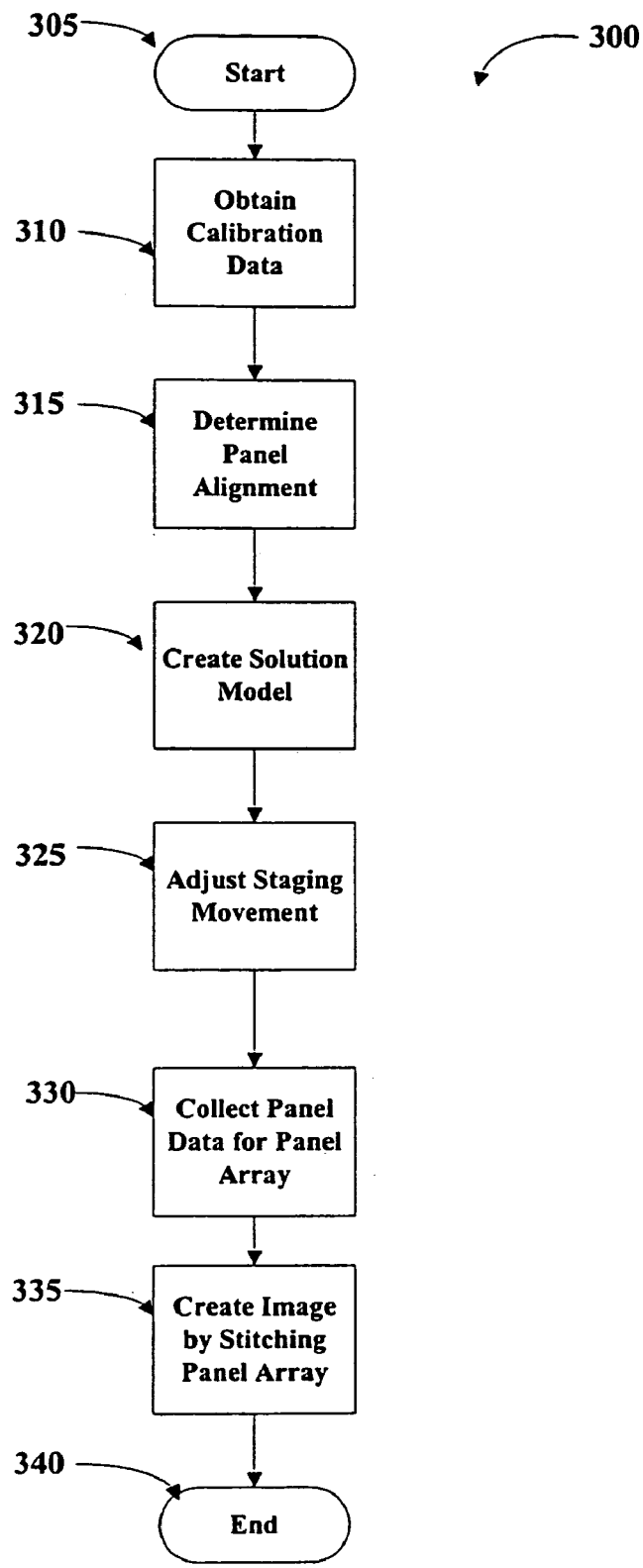
FIG. 3 illustrates the process for calibrating the image system according to the present invention.

Illumination for each panel, typically $\frac{1}{10}$ inch (2.5 mm) square in size, which can, however, vary, is provided by a conventional white light (broad spectrum) source 36. The light (illumination) is directed obliquely to the array as shown in FIG. 3. This eliminates direct reflection of the illumination off the slide, although it is not necessary to the invention. The light from source 36 is applied to a filter 37 and then past a photosensor 44 before reaching the microarray 32. Photosensor 44 is used to measure the total amount of illumination delivered to the small target area (panel) of the microarray during each exposure of the camera. The photosensor measurement is used during a later processing step to correct small variations in light intensity from panel to panel, which typically amount to approximately 5%.

Excitation filter 37 is one of a plurality of filters held in a filter wheel by which a number of different excitation wavelengths can be chosen under software control. In the embodiment shown, the filter wheel may be easily changed; each wheel holds four separate filters. The illumination is provided through a fiber optic cable, which results in a highly consistent pattern of illumination.

Illumination of the array results in fluorescence from the biological specimens in area 33 on slide 34 which is then collected by objective lens 30. Panel 42 encompasses an area in which a total of nine biological specimens are located. The fluorescence data from these nine individual specimens is directed through lens 30, then through an emission filter 35, and then to the CCD camera 38, which detects an image of the array.

Emission filter 35, like filter 37, is one of a plurality of filters held in a filter wheel. As with the illumination filter, emission filter 35 may be selected through software control. In the embodiment shown, the emission filter wheel is easily changeable and may hold up to four emission filter sets.

It is possible that the system response (i.e. the sensitivity and offset) to area 33 may not be absolutely uniform. Each pixel in the image detected by the camera is compensated with gain and offset to produce a uniform response across the image. The response of each pixel is determined by an exposure series. Linear regression analysis of the exposure series data results in gain-offset values for each pixel. This is a common digital microscopy technique and results in all the pixels having the same light intensity, so that all areas of all panels have the same intensity. Images from the CCD camera and illumination information from the photosensor are applied to a processor 47, which will arrange all of the resulting pictures together, as discussed in more detail below.

The light travels from its source 36, through filter 37 and photosensor 44 to the specimens. Fluorescent emissions are collected by the objective lens 30 and passed through filter 35, on their way to the CCD camera 38. Such an optical system is generally conventional and therefore not discussed in detail. The general configuration of such systems, with the exception of oblique illumination, is present in fluorescence microscopes, such as available from Olympus and Nikon, or the assignee of the present invention.

The substrate with the microarray 32 is then moved successively by a precise moving system or stage 48. The initial position of the scanner system relative to the microarray is in one corner of the array referred to by x,y coordinates o,o. It should be understood, however, that the image system could alternatively be moved by a stage, with the array remaining stationary.

In this application, the position of each successive portion or panel of the array is thus known to an accuracy of approximately one picture element (pixel), repeatable to a fraction of a pixel. A very precise staging apparatus is shown in U.S. Pat. No. 5,812,310, owned by the assignee of the present invention and incorporated herein by reference. Such a staging apparatus can easily meet the requirements of the present invention.

Stage 48 is moved successively in the embodiment shown, such that eventually all of the information in the array is obtained, in the form of successive panels, each of which has an identifying set of stage coordinates. The panels are then put together to form a single, unitary image of the complete array by processor 47. With the high precision of the staging apparatus and the software control, which is explained hereinafter, the images can be joined together to form the image of the entire array with minimal or no mathematical processing to achieve alignment. If a geometric alignment of the staging process is performed, it is not necessary to in any way further align the data between adjacent panels or to use computation techniques to string or connect the images together based on particular features of adjacent panels. The complete array thus can be constructed purely on the recorded position of the stage at each collection point, providing coordinate points for each panel are known.

With respect to staging accuracy, in some cases, the x,y axes of the stage are not exactly parallel with the pixel rows and columns in the camera. If the rotation angle between the stage and the camera is known, the camera can be rotated appropriately relative to the stage. The rotation angle can be determined, for instance, by adjusting the rotation angle until adjacent panels are aligned perfectly. The rotation angle, alternatively, can be used in the processing of the images, as explained below.

In addition to the camera and stage rotation, there are other factors that may cause the staging to be misaligned. The exact magnification of the image system may be unknown. Further, because a mechanical device moves the staging area, it is possible that the movements and mechanisms are not completely accurate. For example, the stage perpendicularity may be off slightly. This may result when the angle between the x and y axis is not exactly 90 degrees. For example, a panel may be designed to be nominally 1 mm square. However, during the manufacturing process of the array, the panel may turn out to be 1 mm by 0.9 mm. Without correction, the staging area will leave a gap of 0.1 mm between each panel.

Other factors may cause panel misalignment. A positioning error may be introduced as the staging area is moved in either the x or y direction. In one embodiment of the invention, the staging area is moved with a lead screw system. The lead screw revolves to move the staging area. Although the lead screw is highly accurate, the revolution of the screw may introduce a very slight sinusoidal pattern into the movement. Thus, as the staging area is moved in the x direction, a slight x direction sinusoidal error may be introduced in both the x and y directions. Similarly, when the staging area is moved in the y direction, a slight y direction sinusoidal error may be introduced in the x and y directions. These errors are referred to as a "ripple" error.

The combination of each of the possibilities of panel misalignment creates a situation where the actual panel locations are moved away from the expected panel locations. The present invention calibrates the errors prior to imaging and uses the results of this calibration to adjust the panel locations prior to acquiring the panel images and combining or "stitching" the panels together. By avoiding the panel misalignments, the panel images can be directly stitched because the panels are located in exactly the correct position.

Figure 2A:
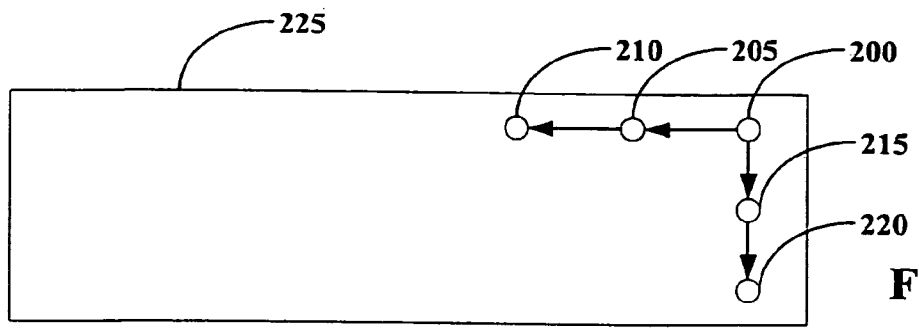
FIG. 2a is a diagram showing calibration data obtained using the stepping data technique according to the present invention.

There are several methods of collecting data to determine the alignment errors. FIG. 2*a* is a diagram showing calibration data obtained using the "stepping data" technique according to the present invention. In stepping data, a small, bright spot 200 is positioned in a corner of the camera image, and the XY location is recorded based on the intensity center. The bright spot may be a data point from a gauge slide 225, or it may be any bright spot the camera can find, such as a speck of dust. The spot is then scanned along a series of points along the X axis 205, 210 with the field of view of the camera. The recorded locations contain information required to solve for the calibration algorithm. The process is then repeated along the Y axis for spots 215, 220.

To improve the best-fit statistics, the process may be repeated at more than one location in the XY travel range. The stepping data process does not require the use of a gauge slide, but is facilitated by the presence of a regular array of bright spots in the XY scan area, thereby making it easier to find the next spot.

Figure 2B:
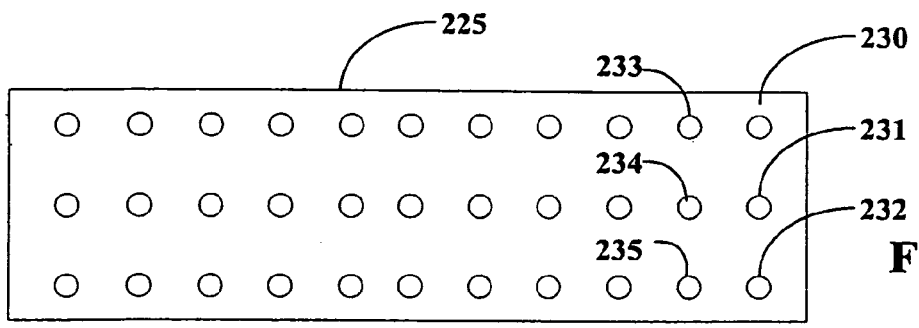
FIG. 2b is a diagram showing calibration data obtained using the slide data technique according to the present invention.

FIG. 2b is a diagram showing calibration data obtained using the "slide data" technique according to the present invention. For slide data, a gauge slide 225 is positioned in the staging area having a series of bright spots 230–235 at predetermined locations. To calibrate, one of the bright spots 230 is positioned at a predetermined location in the camera image. The location is then calculated from the stage motor coordinates. To avoid combining the optical and camera pixel scaling, the spots are always moved to the same pixel coordinates. The next slide data point 231 is then obtained by moving the XY stage such that the next gauge slide spot is located at the predetermined position within the camera image. The motor and gauge slide distance scaling affect the slide data. During a scan to collect slide data, the rotation angle between the camera and the gauge slide should be estimated in order to simplify the search for the spots. In addition, it helps to estimate the slide scale.

Figure 2C:
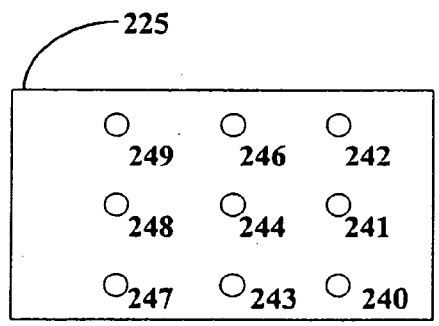
FIG. 2c is a diagram showing calibration data obtained using the sub-spot data technique according to the present invention.

FIG. 2c is a diagram showing calibration data obtained using the "sub-spot" data technique according to the present invention. For sub-spot data, a gauge slide 225 is positioned in the staging area having a series of bright spots 240–248 at predetermined locations. Sub-spot data can be collected when more than one gauge slide spot is visible within a single camera image. Such data are affected by the gauge slide, optical, and camera pixel scale, as well as the rotation angle between the camera and the gauge slide. For every slide data point 240–248, the sub-spot data may be collected for solution of the sub-spot scaling factor. The data may be measured relative to a base sub-spot, such as sub-spot 240.

Figure 2D:
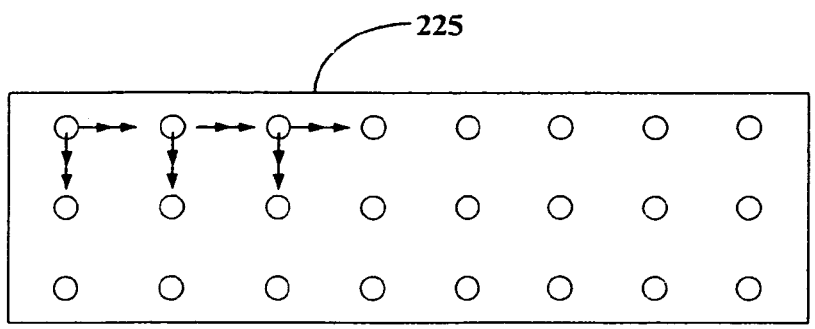
FIG. 2d is a diagram showing calibration data obtained using the absolute data technique according to the present invention.

FIG. 2d is a diagram showing calibration data obtained using the "absolute data" technique according to the present invention. Absolute data may be generated by combining the stepping data and the slide data, and possibly even the sub-spot data. For absolute data, a gauge slide 225 is positioned in the staging area. When obtaining absolute data, the stepping data is used because the gauge slide scaling and rotation are not involved. The dependencies that do exist for stepping data are appropriate for the stage mapping project that is designed to collect panels at well controlled locations. To convert the slide data coordinates to stepping data coordinates, the process divides by the gauge slide scale, rotates by the negative gauge slide angles, and multiples by the optical scale. The absolute data may be used to solve for the ripple parameters.

FIG. 3 illustrates a process 300 for adjusting the imaging system based on the alignment issues. The process begins in a START block 305. Proceeding to block 310, the calibration data is obtained from the imaging system. As described above, there are many different techniques for obtaining calibration data, and any or all of these techniques may be used.

Proceeding to block 315, the panel alignment is determined from the calibration data. The panel alignment may be calculated using the calibration data. For example, to solve for the cross-coupled position ripple along the X and Y axes, the following mathematical solution may be used. Although a sample solution is presented, it can be understood that a solution may be obtained from the calibration data using multiple techniques, and the present invention is not intended to be limited by the solution presented. Using a virtual coordinate inversion technique, where the virtual coordinates are converted to the motor coordinates, or vise-versa, may solve the cross-coupled ripple error. Thus, $(Xm, Ym) \rightarrow (X_c, Y_c)$ or $(X_c, Y_c) \rightarrow (Xm, Ym)$;

where Xm is the X motor position;
Ym is the Y motor position;
Xc is the X virtual position; and
Yc is the Y virtual position.

The calibration can be calculated using the following equation and solution.

$$Xr = Xm + Ax * \sin[2\pi * Fx * Ym + Px];$$

$$Yr = Ym + Ay * \sin[2\pi * Fy * Xm + Py];$$

$$Xs = Xr - Yr * \sin[\gamma];$$

$$Ys = Yr - Yr * \cos[\gamma];$$

$$Xc = Sx * (Xs * \cos[\theta] - Ys * \sin[\theta]); \text{ and}$$

$$Yc = Sy * (Xs * \sin[\theta] - Ys * \cos[\theta]),$$

where Xr and Yr are the ripple coordinates along the respective axis;
Px and Py are the phase shift;
Ax and Ay are the amplitude;
Fx and Fy are the frequency; and
Xs and Ys are intermediate variable used to simplify the equations.

The equations are then solved for {Xm, Ym} as a function of {Xv, Yv}. The equations may be solved using an iterative solution or other estimate technique.

Proceeding to block 320, a solution model is created based on the calibration data. The solution model may be an algorithm which coverts the desired positioning information into the actual positioning information by using the calibration data. One of skill in the art is able to create a solution model after obtaining the calibration data, and thus will not be described herein.

Proceeding to block 325, the movement of the staging area is adjusted based on the solution model. In one embodiment, the staging area is moved under software control, where the software contains the solution model and automatically adjusts the desired ("virtual") positioning information into actual ("motor") positioning information. This process may be transparent to a user.

Proceeding to block 330, panel data is collected for each panel in the panel array. Because the calibration data is used to adjust the staging position, the coordinate positions of each panel will be more precise. Details of the panel data collection are described below.

Proceeding to block 335, a complete image is created by "stitching" together each panel of the panel array. The stitching is described below. The process 300 then terminates in and END block 340.

Figure 4:
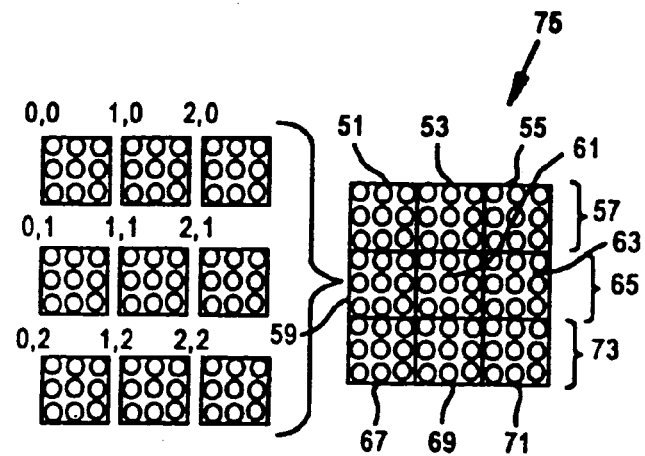
FIG. 4 is a diagram showing the arrangement of data using the system of the present invention.

The "stitching" together of the panels is illustrated in FIG. 4, a nine panel array comprising 3 columns and 3 rows. Panels 51, 53 and 55 comprise an upper row 57; panels 59, 61 and 63 comprise a middle row 65; and panels 67, 69 and 71 comprise a lower row 73. Each panel has specific x,y coordinates indicating its position. The individual panels, imaged by the CCD camera, are arranged together by processor 47 to form a complete image 75 of the array field 32.

Figure 6:
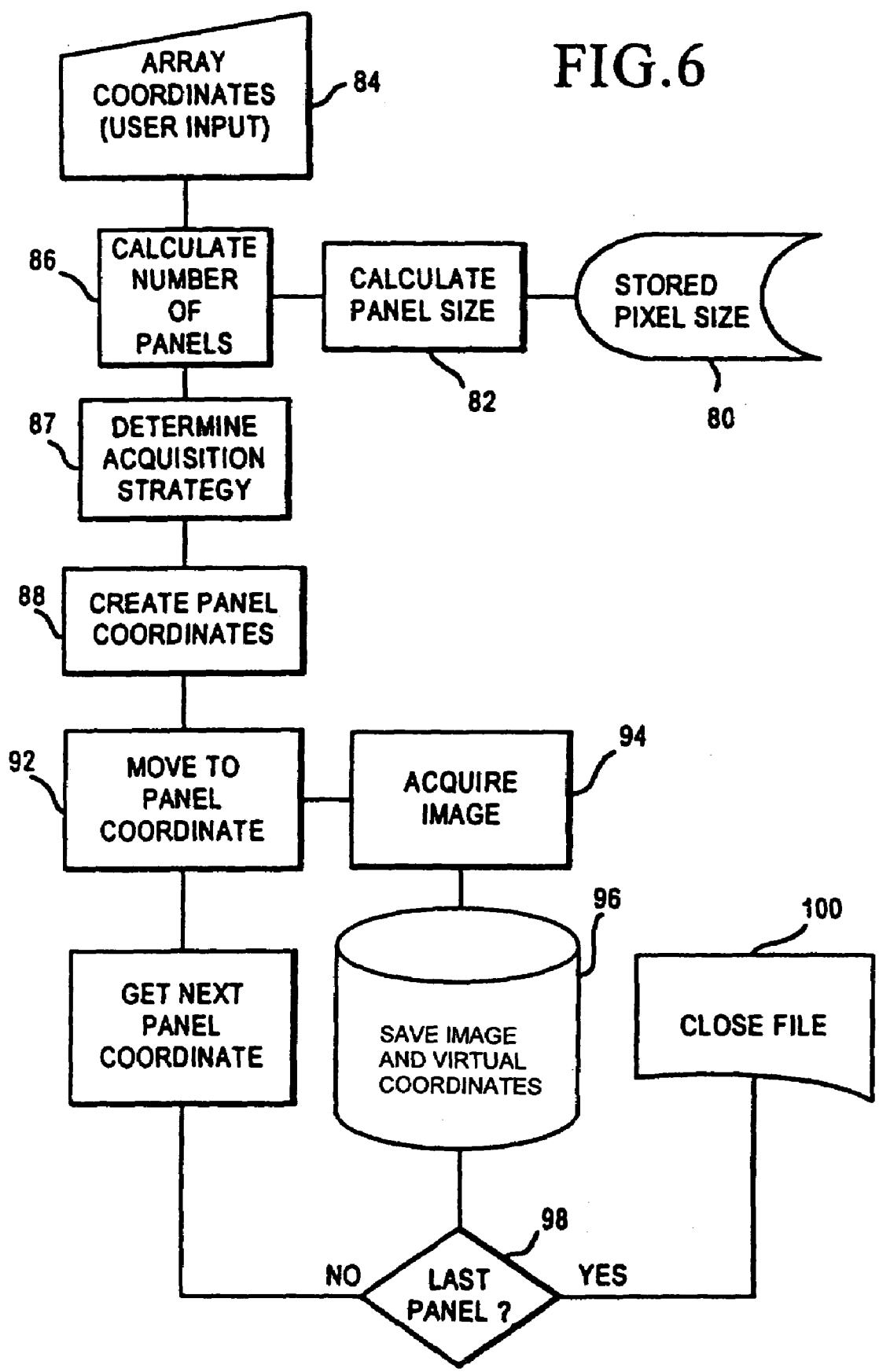
FIG. 6 is a flow chart showing a portion of the software for the present invention.
Figure 7:
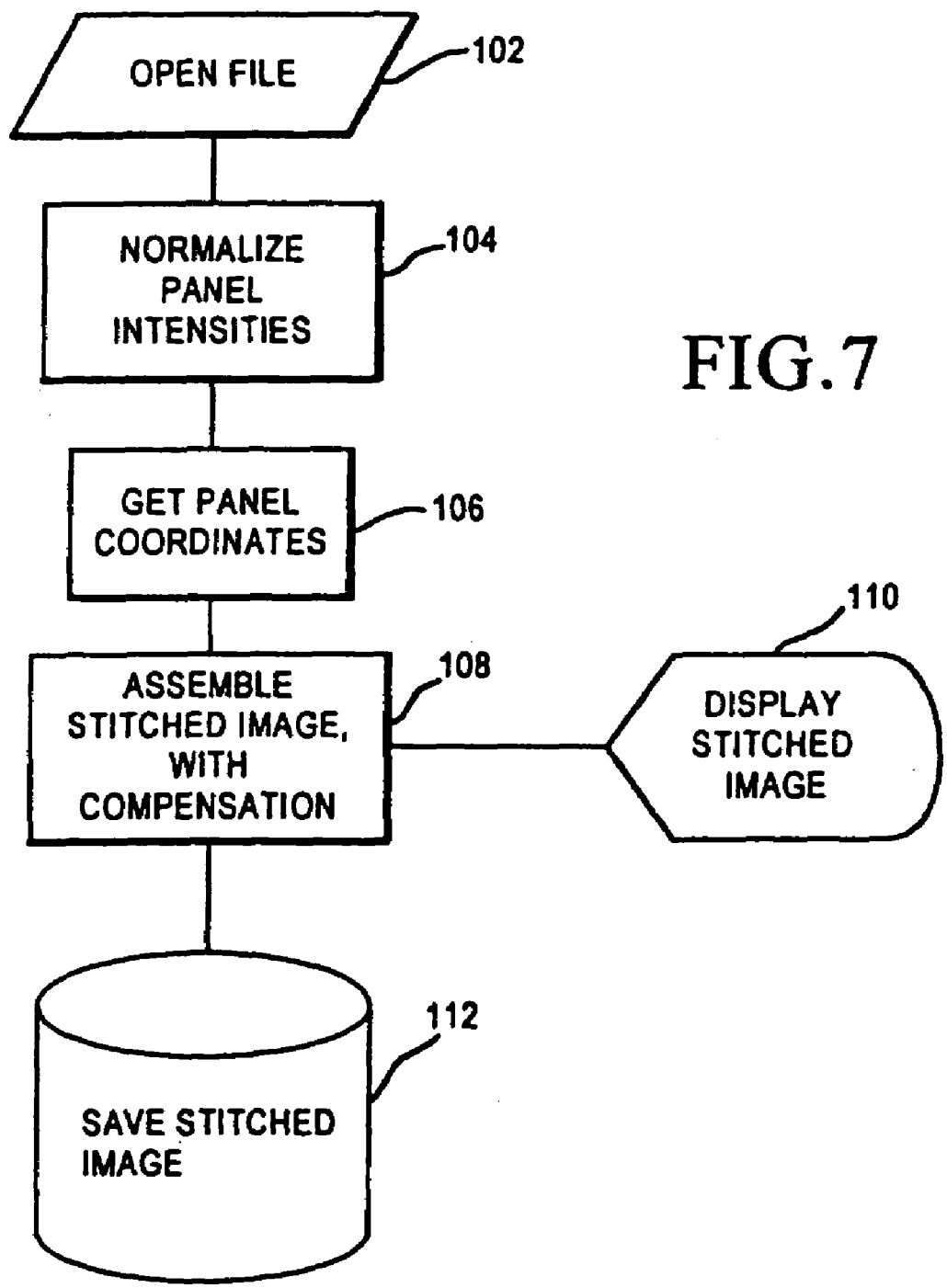
FIG. 7 is a flow chart showing another portion of the software for the present invention.

The process of obtaining the data in sequential steps and arranging the resulting panels together to form the complete image is shown in FIGS. 6 and 7. In FIG. 6, which shows the steps in acquiring the data, the pixel size of the information, which, after calibration, is known and previously stored (block 80), approximately 5 microns in the embodiment shown, is used to calculate the size of the panels (block 82). In the embodiment shown, this would be approximately 2-½×2-½ mm (⅒ inch), although it should be understood that other panel sizes could be used. The accurate determination of pixel size is important to accomplish the arrangement of the various images into a single picture. The number of rows and columns of the camera images and the size of the pixel determine the exact area of a panel. Where a single panel image comprises 500×500 pixels, the pixel size must be accurate to within 0.1% in order to limit placement errors of panels to less than ½ pixel. The pixel size can be stored for use by the processor.

As indicated in FIG. 6, the user provides the coordinates (block 84) for the array on the slide or other substrate. The coordinates in effect identify the actual physical boundaries and thus the size of the array.

From this resulting size of the array, and the calculated panel size, the total number of panels which will comprise the scanned array is then determined, as shown at block 86. Once the number of panels is calculated, then the particular manner in which the slide is maneuvered by the stage assembly to obtain (scan) the entire array is determined, as shown at block 87. For instance, successive images can be obtained in the direction of successive rows, either in one direction, or back and forth, or by successive columns, or some combination thereof. Of course, the calculation of the panel size and total number of panels involves conversion between the virtual and motor coordinates following calibration.

For a particular scan area on a given slide, the location and size of each portion of the area covered by a single image must be determined, as well as the number of portions to cover the entire area. The size of the scan area, the pixel size of the detector, the magnification in the image, and the dimensions of the detector array determine this.

Following the determination of the image acquisition strategy, i.e. pattern, the x,y coordinates (virtual and motor) for each successive panel are then determined, as shown at block 88. The stage is then moved to the x,y motor coordinates of the first panel as shown at block 92, and the image at that position is acquired (block 94), as discussed above. The stage is arranged so that it only moves in x and y directions. It does not move in the z (height) dimension, so as to preserve correct focus over the array.

Figure 5:
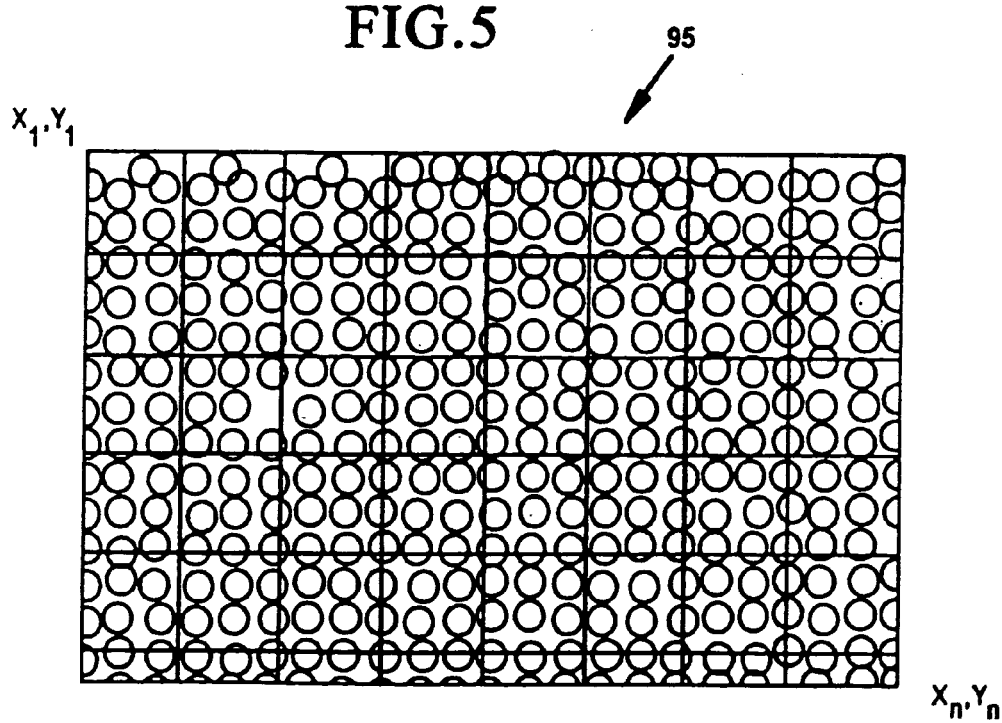
FIG. 5 is a more complete arrangement of the data produced by the system of the present invention for a microarray.

As indicated above, each panel image comprising nine individual biological specimens in the embodiment shown has very high resolution. This first panel image (coordinates $x_1$ $y_1$ in FIG. 5) is then saved as well as the virtual coordinates, as shown at block 96.

If the user has chosen to scan the specimens with more than one wavelength, the filter wheels 35a and 37a are changed to the appropriate excitation/emission filter pair and a new image is acquired and stored having the same coordinates as the first panel. This process may be repeated for any wavelengths that are selected. The stage 48 does not move when the filter pairs are changed so as to minimize chromatic shift in the final, complete image of the microarray. The net effect of this scanning technique is that each panel position may have data with multiple wavelengths, with substantially zero lateral shift between filter (wavelength) pairs.

The software then determines whether the panel just obtained is the last panel in the array, shown at block 98. If not, the stage is moved to the next panel location, as established in the acquisition strategy table. The image is acquired for that panel and that information and its virtual coordinates saved, shown at block 96. This repetitive process continues until all of the panels in the array have been imaged and saved, i.e. until panel $x_n y_n$ in array 95 of FIG. 5, for instance, has been obtained and saved. At this point, the file is closed, as shown at block 100, the acquisition process having been completed.

FIG. 7 shows the processing of the acquired data to produce the whole "stitched together" image of the complete array. In the first step, the file created by the software portion in FIG. 6 is opened, shown at block 102. The light intensities of the panels are normalized, as shown at block 104, to provide uniform values of intensity for each panel relative to each other. This is accomplished with information from the photosensor. Also, conventional techniques of correcting uniformity of illumination, pixel by pixel with gain/offset, known as "flat-fielding", are carried out, as well as making the background intensity patterns of the panels the same, which is known as "panel flattening". These techniques are disclosed in co-owned U.S. patent application Ser. No. 09/771,343, filed Jan. 26, 2001, which is incorporated by reference herein in its entirety.

Thus, the images are normalized over each separate image portion, such as a panel, and also normalized over the entire area being scanned, comprising all of the images. These techniques eliminate any resulting "patched" look for the final, complete image. The virtual x,y coordinates of each panel are then obtained from the file, as shown at block 106. The panels are then assembled according to their specific coordinates, until the complete array image is produced, as shown at block 108. This is repeated for all filter/wavelength pairs collected for that sample. The assembled plurality of panels is then displayed, as shown at block 110. The complete image, with all of the wavelength information, is also saved, as shown at block 112.

Again, the individual separate panels, each comprising a small portion of the array, are simply put together on the basis of their coordinate values and are not mathematically aligned or otherwise altered to fit together. This is because of the precise, calibrated movement capability (with no movement in height) of the stage and the software which makes minor adjustments to illumination intensity and background over each image and over all the images and then assembles the individual panels of data into a complete image.

As indicated above, the present invention is significant in the scanning of biological arrays in that it is quite different from laser scanning methods, which are presently preferred. In the present invention, a full spectrum illumination source is used, along with a conventional scientific grade, cooled CCD camera, with its superior linearity and efficiency. A succession of individual panel images of the complete array of the various wavelengths are produced, with the panels then being pieced together based on the panel x,y coordinates into a complete image of the array.

Although a preferred embodiment of the invention has been disclosed, it should be understood that various changes, modifications and substitutions may be incorporated in such embodiment without departing from the spirit of the invention which is defined by the claims which follow.

What is claimed is:

1. A method of calibrating an imaging system comprising:
    obtaining a sequence of images;
    collecting calibration data from the sequence of images;
    determining positioning and orthogonality errors from the calibration data; and
    creating a solution model for adjusting the imaging system based on positioning and orthogonality data.

2. The method of claim 1, further comprising modifying the position of an image area based on the solution model.

3. The method of claim 1, further comprising modifying the positioning of a mechanical system to compensate for errors based on the solution model.

4. The method of claim 1, further comprising determining calibration data based on stepping data.

5. The method of claim 1, further comprising determining calibration data based on slide data using a reference slide.

6. The method of claim 1, further comprising determining calibration data based on sub-spot data.

7. The method of claim 1, further comprising determining calibration data based on absolute data.

8. A method of obtaining an image of a plurality of specimens comprising:
 determining calibration data;
 creating adjustment parameters based on the calibration data;
 applying the adjustment parameters to position a first portion of the plurality of specimens within a scan area;
 obtaining an image of the first portion of the plurality of specimens;
 applying the adjustment parameters to position a second portion of the plurality of specimens within a scan area;
 obtaining an image of the second portion of the plurality of specimens; and
 combining the image of the first portion and the image of the second portion to create the image of the plurality of specimens.

9. The method of claim 8, further comprising:
 obtaining an image of a plurality of portions of the plurality of specimens, wherein a location of each of the plurality of portions is adjusted based on the adjustment parameters; and
 stitching together each of the images of the plurality of portions of the plurality of specimens.

10. The method of claim 8, further comprising determining calibration data based on stepping data.

11. The method of claim 8, further comprising determining calibration data based on slide data using a reference slide.

12. The method of claim 8, further comprising determining calibration data based on sub-spot data.

13. The method of claim 8, further comprising determining calibration data based on absolute data.

14. A system for scanning a plurality of specimens arranged within a scan area comprising:
 a staging area which moves relative to a camera, the camera being operative to detect images;
 a processor which collects positional and orthogonality calibration data from the staging area, wherein the processor creates an adjustment algorithm to modify movement of the staging area to compensate for the calibration data.

15. The system of claim 14, wherein the calibration data is based on a bright spot within the scan area.

16. The system of claim 14, wherein the staging area is positioned to collect a plurality of images, each of the plurality of images comprising a portion of the total desired image.

17. The system of claim 16, wherein each of the plurality of images is assembled to form the total desired image.

18. The system of claim 14, wherein the calibration data is obtained without the use of a reference slide.

19. The system of claim 14, wherein the calibration data is obtained with the use of a reference slide.

20. The method of claim 1 wherein the sequence of images is captured by a camera.

* * * * *